United States Patent [19]

Johnston et al.

[11] 4,236,912
[45] Dec. 2, 1980

[54] QUINOLINYLOXYPHENOXY AND QUINOLYINYLTHIOPHENOXY ALKANOIC ACIDS AND DERIVATIVES THEREOF AND METHODS OF HERBICIDAL USE

[75] Inventors: Howard Johnston, Walnut Creek; Lillian H. Troxell, Antioch, both of Calif.; Jon S. Claus, Arlington Heights, Ill.

[73] Assignee: The Dow Chemical Company, Midland, Mich.

[21] Appl. No.: 17,753

[22] Filed: Mar. 5, 1979

[51] Int. Cl.³ .................. A01N 43/42; C07D 215/22; C07D 215/36

[52] U.S. Cl. .......................................... 71/94; 71/76; 546/157

[58] Field of Search ....................... 71/94, 76; 546/157

[56] References Cited

U.S. PATENT DOCUMENTS

| | | | |
|---|---|---|---|
| 3,849,420 | 11/1974 | Tong | 71/94 X |
| 4,046,553 | 9/1977 | Takahashi et al. | 71/94 |
| 4,105,435 | 8/1978 | Nishiyama et al. | 71/94 |
| 4,133,675 | 1/1979 | Schurter et al. | 71/94 |

FOREIGN PATENT DOCUMENTS 2546845  4/1977  Fed. Rep. of Germany .............. 71/94

OTHER PUBLICATIONS

Johnston et al., European Patent Application No. 483, published 02/07/79.

Primary Examiner—Donald G. Daus
Assistant Examiner—Diana G. Rivers

[57] ABSTRACT

Novel 2-quinolinyloxyphenoxy and 2-quinolinylthiophenoxy alkanoic acids, amides, salts, and esters thereof, and nitriles derived therefrom and 2-quinolinyloxy- and thio-phenoxy propanols and esters and ethers thereof having the following formula

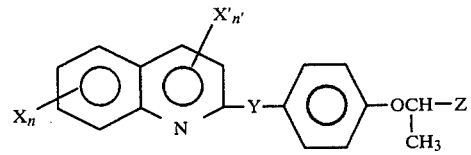

wherein:

X and X' are independently F, Cl, Br, I, —CF₃, CH₃O—, —NO₂, or —N(R')₂, with the proviso that both cannot be —CF₃, CH₃O—, —NO₂, or —NR'₂, n is 0, 1, or 2 and n' is 0 or 1, Y is O or S, Z is —CO₂H, —CO₂M, —CO₂R, —COSR, —CONR'₂, —CSNH₂, —CN, —CH₂OR' or —CH₂O₂CR', M is Na, K, Mg, Ca or —N(R")₄, R" is H, C₁–C₄ alkyl or C₂–C₃ hydroxyalkyl, each R' is independently H or C₁–C₄ alkyl and R is C₁–C₈ alkyl or C₃–C₆ alkoxyalkyl, are useful as herbicidal agents.

Novel 2-quinolinyloxyphenols and 2-quinolinylthiophenols and simple metal salts thereof are useul in the preparation of the aforementioned active compounds.

34 Claims, No Drawings

QUINOLINYLOXYPHENOXY AND QUINOLYINYLTHIOPHENOXY ALKANOIC ACIDS AND DERIVATIVES THEREOF AND METHODS OF HERBICIDAL USE

BACKGROUND OF THE INVENTION

1. Field of the Invention

The invention relates (a) to novel 2-quinolinyloxyphenoxy 2-propanoic acids, salts and esters thereof and 2-quinolinyloxyphenoxy 2-propanols and esters and ethers thereof, and propionitriles, and the corresponding 2-quinolinylthiophenoxy 2-propanoate and 2-propanol compounds, (b) to herbicidal compositions of such novel compounds and (c) to preemergent and postemergent methods of using such compounds for the control of grassy weeds in non-crop areas as well as in the presence of some specified valuable crops. The invention also relates to novel 2-quinolinyloxyphenol and 2-quinolinylthiophenol compounds which are useful in the preparation of the aforementioned active compounds.

2. Description of the Prior Art

Belgian Pat. No. 834,495, issued Feb. 2, 1976, as well as the published German patent application equivalent thereto, viz., No. 2,546,251, published Mar. 29, 1976, describe 2-((4-pyridinyl-2-oxy)phenoxy)alkanoic acids, salts and esters having halo substitution in the 3 and/or 5 ring positions in the pyridine ring. Published Japanese patent application No. 129,313/75, filed in Japan Oct. 29, 1975 teaches pyridyloxyphenoxypropanols and esters thereof, while published Japanese patent application No. 064,160/75, filed May 30, 1975, teaches pyridyloxyphenoxypropionitrile compounds. These prior art compounds are disclosed to be active herbicides useful in the control of grassy weeds.

SUMMARY OF THE INVENTION

The present invention is directed to novel 2-quinolinyloxyphenoxy and 2-quinolinylthiophenoxy alkanoic acids, amides, salts, and esters thereof, and nitriles derived therefrom and 2-quinolinyloxy- and thiophenoxy propanols and esters and ethers thereof having the following formula

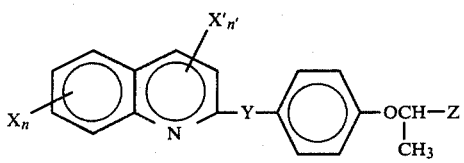

wherein:
X and X' are independently F, Cl, Br, I, —CF$_3$, CH$_3$O—, —NO$_2$, or —N(R')$_2$, with the proviso that both cannot be —CF$_3$, CH$_3$O—, —NO$_2$, or —NR'$_2$,
n is 0, 1, or 2 and n' is 0 or 1,
Y is O or S,
Z is —CO$_2$H, —CO$_2$M, —CO$_2$R, —COSR, —CONR'$_2$, —CSNH$_2$, —CN, —CH$_2$OR' or —CH$_2$O$_2$CR',
M is Na, K, Mg, Ca or N(R")$_4$,
R" is H, C$_1$–C$_4$ alkyl or C$_2$–C$_3$ hydroxyalkyl, each R' is independently H or C$_1$–C$_4$ alkyl and R is C$_1$–C$_8$ alkyl or C$_3$–C$_6$ alkoxyalkyl, which are useful as herbicidal agents.

The invention is also directed to novel 2-quinolinyloxyphenoxy and quinolinylthiophenoxy compounds and salts thereof useful in preparing the aforementioned active compounds and having the following formula:

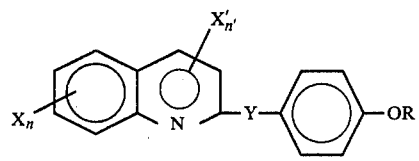

wherein:
X and X' are independently F, Cl, Br, I, CF$_3$—, CH$_3$O—, —NO$_2$, or —N(R')$_2$; with the proviso that both cannot be CF$_3$—, CH$_3$O—, —NO$_2$ or —N(R')$_2$;
n is 0, 1 or 2;
n' is 0 or 1;
Y is 0 or S;
and R is H or Na or K.

Preferred compounds are represented by the formula:

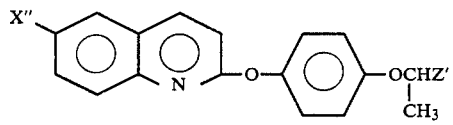

wherein: X" is halogen, and Z' is —CO$_2$H, —CO$_2$M or —CO$_2$R.

The foregoing compounds are used according to the methods of the invention for the control of undesired vegetation, particularly grassy weeds, advantageously in the presence of many valuable crops. Some of the compounds are more useful in postemergent applications while the others are highly useful in preemergent operations as well.

The compounds of the above formula, hereinafter referred to for convenience as "active ingredients", have been found to be especially active as herbicides for the control of undesired vegetation, specifically, grassy or graminaceous weeds including perennial grassy weeds. Accordingly, the present invention also encompasses compositions containing one or more active ingredients as well as preemergent and postemergent methods of controlling undesired plant growth, especially in the presence of valuable crops, and, suprisingly including grassy crops. Such methods comprise applying a herbicidally-effective amount of one or more active ingredients to the locus of the undesired plants, that is, the seeds, foliage, rhizomes, stems and roots or other parts of the growing plants or soil in which the plants are growing or may be found.

DETAILED DESCRIPTION OF THE INVENTION

The term "herbicide" is used herein to mean an active ingredient which controls or adversely modifies the growth of plants because of phytotoxic or other effects substantial enough to seriously retard the growth of the plant or further to damage the plant sufficiently to kill the plant.

By "growth controlling" or "herbicidally-effective" amount is meant an amount of active ingredient which causes a modifying effect and includes deviations from natural development, killing, desiccation, retardation, and the like.

The term "plants" is meant to include germinant seeds, emerging seedlings, as well as established vegetation.

The terms "$C_1$–$C_4$ alkyl" or "$C_1$–$C_8$ alkyl", refer to different size alkyl groups which may be straight or branched.

The term "$C_3$–$C_6$ alkoxyalkyl", is meant to refer to an alkoxyalkyl group having three to six carbon atoms, the alkyl portion being straight or branched The active ingredients of the present invention are generally oils or crystalline solids at ambient temperatures which are soluble in many organic solvents commonly employed as herbicidal carriers.

The 2-quinolinyloxyphenoxypropionic acids may be prepared by reacting the appropriately substituted 2-haloquinoline with the disodium salt of 2-(4-hydroxyphenoxy)propionic acid in a suitable solvent medium, usually dimethylsulfoxide, although in many cases other solvents such as dimethylformamide, hexamethylpyrophosphoramide or tetrahydrofuran might be used. If the appropriately substituted carbostyril is available, this can easily be converted to the 2-chloro derivate by refluxing with phosphorous oxychloride. Direct chlorination of carbostyril in glacial acetic acid followed by reaction with $POCl_3$ gives the 2,3,6-trichloroquinoline. Bromination of carbostyril under similar conditions gives the 6-bromocarbostyril.

If the desired quinoline is available and is unsubstituted at the 2-position, then it can be converted to the 2-chloro-derivative in three steps:

The N-oxide is first prepared by reaction of the quinoline with 30% hydrogen peroxide in acetic acid or trifluoroacetic acid followed by reaction with benzoyl chloride and aqueous sodium hydroxide to give the carbostyril and finally conversion to the 2-chloro derivative by refluxing with $POCl_3$. 2-Bromo-derivatives are prepared in a similar manner.

In some cases the quinoline ring itself must be synthesized and this may be done using the well known Skraup reaction (Org. Syn., Coll. Vol. I, 478).

The active ingredients, i.e., new compounds of the present invention wherein Y is oxygen are readily prepared by the reaction of 4-hydroxyphenoxy-2-propanoic acid or an ester thereof with the desired 2-haloquoinoline.

The new compounds of the present invention wherein Y is sulfur may be similarly prepared by the reaction of 4-mercaptophenoxy-2-propanoic acid or an ester thereof with an appropriate 2-haloquinoline in substantially the same manner as described above but are preferably prepared by reacting the desired 2-haloquinoline with 4-mercaptophenol under basic conditions.

The reaction between such quinoline and the said hydroxy- or mercapto-phenoxy propanoic acid is rather readily carried out in a polar solvent such as dimethyl sulfoxide (DMSO) to which has been added a small amount of aqueous or powdered sodium hydroxide. Reaction is usually carried out at a temperature in the range of about 70° to about 125° C. over a period of about 1 to 3 hours under ambient atmospheric pressure. The reaction mixture is then allowed to cool and is poured into a quantity of cold water and acidified with hydrochloric acid, whereupon the product precipitates and is separated and purified as may be required.

The propanoate esters of the present invention may be prepared in substantially the same manner as set forth above for the propanoic acids, using the requisite ester of 4-hydroxyphenoxy-2-propanoic acid and 4-mercaptophenoxy-2-propanoic acid to react with the appropriate 2-haloquinoline. Or, if desired, the appropriate propanoic acid of the invention is esterified by first converting to the acid chloride with thionyl chloride and then reacting the acid chloride with the appropriate alcohol, or, mercaptan, such as, ethyl mercaptan, propyl mercaptan or butyl mercaptan, according to generally accepted procedures or the classic method of reacting an alcohol and an acid in the presence of a little sulfuric acid may be followed.

The propanoic acid compounds of the invention after conversion to the acid chloride may also be reacted with (a) ammonia to form the simple amide, (b) with an alkyl amine to form an N-alkyl amide or N,N-dialkyl amide, or (c) with a methoxy amine to form an alkoxy amide.

The simple amide serves as preferred starting material for the manufacture of the present nitriles, which are obtained upon reaction of the amide with phosphorous oxychloride.

The propanoate metal salts of the invention are prepared from the propanoic acid form of the compound by simply reacting the carboxylic acid with the requisite inorganic base, such as NaOH, KOH, $Ca(OH)_2$ or $Mg(OH)H_2$. The amine salts are prepared by reacting the propanoic acid compound with the requisite amine, for example, dimethylamine, triethanolamine or trimethylamine, or ammonia.

The compounds according to the invention which are substituted propanols are prepared preferably from one of the above described esters of the propanoic acid form of the compound, such as the methyl ester, by reaction of the ester with sodium borohydride in a polar solvent medium such as methanol, reaction being carried out at a temperature below about 30° C. during an initial period of 1 to 2 hours after which the temperature is brought to about 50° to 60° C. and the solvent then stripped off. The reaction product is then admixed with water and extracted with a water-immiscible organic solvent. Removal of the solvent leaves an oily product.

Esterification of such alcohol is carried out according to methods generally known in the art in which, e.g., an acid chloride is reacted with the alcohol in solvent medium in the presence of a hydrogen chloride acceptor, such as triethylamine. The hydrochloride salt is filtered off and the solvent stripped, leaving an oily product.

Ethers of the alcohols of the invention may be prepared by reacting the alcohol with, e.g., sodium hydride, in a polar solvent such as dimethyl formamide at a temperature of about 35° to 60° C., after which an alkyl bromide is added to the reaction mixture and heated to 75° to 100° C. for one to two hours. The solvent medium is then stripped off under reduced pressure and the crude product is poured into cold water and final product taken up with water immiscible solvent such as heptane. The solvent, on being stripped off, leaves an oily product.

In an alternate process for making the present propanoic acid compounds, a salt, e.g., the sodium salt, of 4-methoxyphenol, 4-mercaptophenol or 4-mercaptoanisole is dissolved in a solvent such as dimethyl sulfoxide and the requisite 2-haloquinoline is added to the solution of the methoxy phenol or methoxy phenyl mercaptide and reacted in the presence of a little aqueous sodium hydroxide at a temperature in the range of about 70° to 130° C. and over a time interval of about 30 to 45 minutes. The reaction mixture is then cooled somewhat and poured over ice. The solid product is filtered off and washed with water and taken up in a solvent mixture and reprecipitated therefrom. The methoxy group, if present, is then cleaved off the phenyl ring by refluxing the compound in 48% by weight HBr for about an hour and after purification, the phenolic product is precipitated from acidic solution and recovered, as by filtration, and dried. The resulting quinolinyloxy- or quinolinylthio-phenol is then dissolved in a solvent such as dimethyl sulfoxide, anhydrous powdered sodium hydroxide is added thereto and reacted therewith for a few minutes at about 75° to 85° C. Then a lower alkyl ester, such as the ethyl ester of 2-bromopropanoic acid, is added to the reaction mixture and stirred for a time, such as about half an hour, at approximately 100° C. or up to about 2 hours in the case of the sulfur bridged compound. The reaction mixture is then allowed to cool and poured over ice or simply into cold water whereupon an oily layer separates which can be recovered by conventional techniques, such as, taking up in a water-immiscible solvent and subsequently stripping the solvent off leaving an oily product. The product so obtained will be the alkyl ester of the propanoic acid compound. The acid may be obtained by hydrolysis.

In carrying out the several reactions of this alternate process, the reactants are usually mixed with a carrier medium, such as, for example, methylethyl ketone, methylisobutyl ketone or an aprotic polar solvent such as dimethylformamide, dimethylacetamide, dimethylsulfoxide (DMSO), N-methylpyrrolidone, hexamethylphosphoramide or sulfolane. The first step condensation is generally carried out at a temperature of at least 50° C., preferably about 70° to about 150° C. and during a reaction period of about 1 to about 20 hours, preferably about 1 to about 10 hours. The second condensation reaction is carried out under similar reaction conditions except that the reaction is usually accomplished in a shorter period of time such as about 0.5 to 10 hours, typically using one of the aprotic solvents such as dimethylsulfoxide as reaction medium. The dealkylation step, where employed, is carried out using as a suitable dealkylation agent, a hydro acid such as hydrobromic acid or hydriodic acid employed as a concentrated aqueous solution of about 40 to about 60 percent by weight concentration. Reaction is carried out at a reflux temperature which usually falls in the range of about 75° to about 150° C. but preferably is about 100° to 140° C. The dealkylation reaction is generally completed in about 1 to about 10 hours.

The active ingredients of the above formula wherein Z is —CH$_2$OH are readily prepared from the requisite 2-propanoic acid compound, prepared as described above, followed by esterification with a primary alcohol conveniently available, such as methanol, and in the presence of a small amount of sulfuric acid, after which the ester is reduced to the alcohol, for example, upon reaction with sodium borohydride in aqueous medium and at close to ambient room temperature. After removal of excess primary alcohol the product may be isolated, for example, by extraction from the reaction mixture with a water-immiscible solvent or solvent mixture such as methylene chloride-heptane. Finally, the solvent is stripped off and removed under reduced pressure leaving the product which is usually an oil.

The so-produced substituted propanol is esterified, if desired to make an active ingredient of the above formula wherein Z is —CH$_2$OOCR', e.g., by reacting it with the acid chloride of the esterifying organic acid in solvent medium, such as toluene, containing in admixture, an HCl acceptor such as triethylamine. Reaction proceeds steadily over about a 1 to 1.5 hour period at a temperature in the range of about 100° to about 135° C. The precipitated trialkylamine hydrochloride is filtered off and the solvent medium stripped off. Subsequently, the residue is preferably washed with water and then taken up in hot heptane, dried, and the heptane distilled off leaving an oily product.

The substituted propionitriles of the invention are prepared using the propanoic acid compound as the starting material. The carboxylic acid is reacted with thionyl chloride to form the acid chloride which is in turn reacted with NH$_4$OH to produce the amide. The amide is reacted with POCl$_3$ to form the nitrile.

The following examples illustrate the present invention and the manner in which it can be practiced but as such are not to be construed as limitations upon the overall scope of the invention.

EXAMPLE 1

2-Chloro-6-fluoroquinoline

6-Fluoroquinoline-1-oxide (9.25 gm, 0.057 mole) was suspended in 130 ml of water. Benzoyl chloride (8.4 gm, 0.06 mole) and a solution of sodium hydroxide (5.3 gm) in 45 ml of water were added alternately in small portions over a 45 min. period keeping the temperature at about 25° C. After all reagents had been added the mixture was stirred for 1.5 hr. and the solid filtered off and dried in toluene. The yield was 3.0 gm of material which was used without further purification for the next step.

A mixture of the so-prepared 6-fluorocarbostyril (2.9 gm, 0.018 mole) and 30.0 ml of phosphorous oxychloride was refluxed for 1.5 hr. Most of the excess phosphorous oxychloride was then distilled off under aspirator vacuum and the residue poured over crushed ice. The reaction mixture was made nearly neutral with 50% sodium hydroxide. The crude solid product was collected by filtration, taken up in m.p. 104°–105°

Yield: 2.8 gm

Analysis: Calc: C-59.52; H-2.77; N-7.71; Cl-19.53; Found: C-59.24; H-2.86; N-7.50; Cl-19.62

2-(4-((6-Fluoro-2-quinolinyl)oxy)phenoxy)propionic acid 2-(4-Hydroxyphenoxy)propionic acid (2.5 gm, 0.0127 mole) was dissolved in 50 ml of DMSO. A solution of sodium hydroxide (1.04 gm, 0.026 mole) in 3.0 ml of water was added and the mixture was stirred for a few minutes to insure complete conversion to the disodium salt. 2-Chloro-6-fluoroquinoline (2.5 gm, 0.0137 mole) was dissolved in 45.0 ml of DMSO and then added all at once to the sodium phenate solution. The reaction mixture was then heated to 125° C. and stirred under nitrogen at this temperature for 1.5 hr. At the end of this time it was cooled and poured into 400 ml of cold water. The aqueous mixture was washed with methylene chloride to remove a small amount of insolubles present and the aqueous layer was separated and acidified to pH 1 with concentrated hydrochloric acid. The phenoxy acid liberated was extracted with methylene chloride. Removal of the solvent left the crude product which was taken up in hot toluene, dried with sodium sulfate and decolorized with "Norite". After removal of about two-thirds of the volume of toluene and addition of hexane, the product, 2-(4-((6-fluoro-2-quinolinyl)oxy)-phenoxy)propionic acid, precipitated as a white solid.
m.p. 148°–150°
Wt. 3.1 gm
Analysis: Calc: C-66.05; H-4.31; N-4.28; Found: C-65.93; H-4.33; N-4.23

EXAMPLE 2

2-(4-(2-quinolinyloxy)phenoxy)propanoic acid

The disodium salt of 2-(4-hydroxyphenoxy)propionic acid was made by dissolving the acid (9.1 gm, 0.05 mole) in 50 ml of DMSO and adding a solution of sodium hydroxide (4.4 gm, 0.11 mole) in 13 ml of water. The mixture was stirred for 30 min. and warmed to 55° C. at which time a solution of 2-chloroquinoline (8.2 gm, 0.050 mole) in 20 ml of DMSO was added. The reaction mixture was heated at 97°–108° for 1.5 hr. and then at 122°–125° for one hour longer. At the end of this time the mixture was poured into 600 ml of cold water and acidified. It was allowed to stand until solids formed which were taken up in toluene. From this 6.5 gm of 2-(4-(2-quinolinyloxy)phenoxy)propanoic acid were obtained.
m.p. 182°–184°
Analysis: Calc: C-69.89; H-4.89; N-4.53; Found: C-70.33; H-5.04; N-4.51

EXAMPLE 3

2-(4-((6-Chloro-2-quinolinyl)oxy)phenoxy)propionic acid 2-(4-Hydroxyphenoxy)propionic acid (2.85 gm, 0.0156 mole) was dissolved in 60 ml of dimethylsulfoxide. A solution of sodium hydroxide (1.25 gm, 0.031 mole) in 2.0 ml of water was added and the mixture stirred for a few minutes to insure complete conversion to the disodium salt. 2,6-Dichloroquinoline (3.1 gm, 0.0126 mole) was dissolved in 50 ml of DMSO and then added all at once to the sodium phenate solution. The reaction mixture was then heated to about 125° C. and stirred at this temperature for 3.0 hours. At the end of this time it was cooled, poured into 350 ml of cold water and acidified with concentrated hydrochloric acid. The precipitated crude product was collected on a filter, washed with fresh water, sucked damp dry and taken up in hot toluene. It was then dried over sodium sulfate, treated with "Norite", filtered and the filtrate concentrated and chilled to precipitate the white crystalline 2-(4-((6-chloro-2-quinolinyl)oxy)phenoxy)propionic acid.
m.p. 169°–171°
Yield: 3.05 gm
Analysis: Calc: C-62.89; H-4.10; N-4.07; Cl-10.31; Found: C-62.48; H-4.19; N-3.77; Cl-9.74

EXAMPLE 4

2-(4-((6-Bromo-2-quinolinyl)oxy)phenoxy)propionic acid 0.07 Mols (10.16 g) of carbostyril were put into 100 ml acetic acid in a 500 ml round bottom flask fitted with an air stirrer, thermometer and a vented dropping funnel. It was stirred and warmed to 56° C. where the carbostyril was in solution. 0.075 Mols (12.0 g) of bromine were put into 50 ml of acetic acid and added to the reaction over a one hour period. The temperature was held between 56° and 65° C. The reaction was then stirred for 1¾ hr. at 63°–65° C. It was then cooled to 38° C. and the solids filtered off. From this and the filtrate were obtained 7.65 g of 6-bromocarbostyril (product checked by IR). A second fraction of 3.9 g was also obtained which looked to be a mixture of monobromo and dibromocarbostyril.

42 g (0.156 M) of phosphorous tribromide were put into a heavy walled long test tube and warmed to 70° C. at which time 4.0 g (0.025 M) of bromine were added. This was heated to 120° C. where the mixture turned liquid. The monobromocarbosytril was then spooned in. The temperature rose to 140° C. It was taken on up to 160° C. The reaction mixture was cooled to about room temperature and scooped out into ice. The product was taken up in hexane and crystallized. From this 4.1 g of product were isolated which had an elemental analysis of:
Calc: C-37.57; H-1.78; N-4.78; Br-56.62; Found: C-37.66; H-1.76; N-4.88; Br-55.70
This material had a melting point of 162°–165° C.

The disodium salt of 2-(4-hydroxyphenoxy)propionic acid was made by dissolving the acid (4.5 gm, 0.0247 mole) in 50 ml of DMSO and adding a solution of sodium hydroxide (2.0 gm, 0.05 mole) in 6.5 ml of water. The mixture was stirred for 25 min. and warmed to 55° C. at which time a solution of 2,6-dibromoquinoline (6.5 gm, 0.02265 mole) in 60 ml of DMSO was added. The reaction mixture was warmed to 80° C. over a 20 min. period, then up to 87° C. in an additional 70 min. In was then poured into 300 ml of cold water, acidified and let stand until the precipitate solidified. On purification 6.25 gm of 2-(4-((6-bromo-2-quinolinyl)oxy)phenoxy)propionic acid were obtained which melted at 167°–168.5° C.
Analysis: Calc: C-55.68; H-3.64; N-3.61; Br-20.58; Found: C-55.63; H-3.72; N-3.54; Br-20.44

Employing the above described procedures, the following compounds were prepared by reacting 2-(4-hydroxyphenoxy)propionic acid with the desired 2-chloroquinoline:

| Product | m.p. | Analysis Calc. | Found |
|---|---|---|---|
| 2-(4-((3,6-dichloro-2-quinolinyl)oxy)phenoxy)-propionic acid | 180–182° C. | C-57.16 | 57.14 |
|  |  | H-3.46 | 3.60 |
|  |  | N-3.70 | 3.70 |
|  |  | Cl-18.75 | 18.64 |
| 2-(4-((6-chloro-2-quinolinyl)-oxy)phenoxy)propionic acid | 169–171° C. | C-62.89 | 62.48 |
|  |  | H-4.10 | 4.19 |
|  |  | Cl-10.31 | 9.94 |
|  |  | N-4.07 | 3.97 |
| 2-(4-((6-fluoro-2-quinolinyl)-oxy)phenoxy)propionic acid | 148–150° C. | C-66.05 | 65.50 |
|  |  | H-4.31 | 4.33 |
|  |  | N-4.28 | 3.78 |

Also, 2-(4-((6-bromo-2-quinolinyl)thio)phenoxy)propionic acid, m.p. 163°–169° C., was prepared by reacting 2,6-dibromoquinoline with 4-mercaptophenol as described hereinbefore. The corresponding 6-chloro substituted analog is among the preferred embodiments of the invention.

The other acids, esters, amides, nitriles, ethers, alcohols and esters of alcohols of the invention are prepared in a manner similar to that illustrated above for the respective types of compounds.

The compounds of the present invention have been found to be suitable for use in methods for the pre and postemergent control of annual and perennial grassy weeds. The active ingredients of the present invention have been found to have advantage over prior art compounds in the control of perennial grassy weeds in that the present compounds control a broader spectrum of such weeds than the counterpart compounds while exhibiting a higher level of activity or control at like dosage rates. In addition, most broad leafed crops and many grassy crops are sufficiently tolerant towards the present compounds that grassy weeds, including perennial grassy weeds may be controlled therein particularly with the preferred compounds of this invention.

For all such uses, unmodified active ingredients of the present invention can be employed. However, the present invention embraces the use of a herbicidally-effective amount of the active ingredients in composition form with an inert material known in the art as an agricultural adjuvant or carrier in solid or liquid form. Such adjuvants or carriers must not be phytotoxic to valuable crops particularly at the concentration employed in applying the composition in attempting selective weed control in the presence of crops. If weed control is desired in the absence of crops, it is generally sufficient to employ adjuvants or carriers which do not leave a persistant phytotoxic residue.

Thus, for example, an active ingredient can be dispersed on a finely-divided solid and employed therein as a dust. Also, the active ingredients, as liquid concentrates or solid compositions comprising one or more of the active ingredients can be dispersed in water, typically with aid of a wetting agent, and the resulting aqueous dispersion employed as a spray. In other procedures, the active ingredients can be employed as a constituent of organic liquid compositions, oil-in-water and water-in-oil emulsions or dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

As organic solvents there can be employed, e.g., toluene, xylene, kerosene, diesel fuel, fuel oil, and petroleum naptha, ketones such as acetone, methylethyl ketone and cyclohexanone, chlorinated hydrocarbons such as trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butylcarbitol acetate and glycerine. Mixtures of water and organic solvents, either as emulsions or solutions, can be employed.

The active ingredients can also be applied as aerosols, e.g., by dispersing them by means of a compressed gas such as one of the hydrocarbon successors to the fluorocarbons which are shortly to be banned.

The active ingredients of the present invention can also be applied with solid adjuvants or carriers such as talc, pyrophyllite, synthetic fine silica, attapulgus clay, kieselguhr, chalk, diatomaceous earth, lime, calcium carbonate, bentonite, Fuller's earth, cotton seed hulls, wheat flour, soybean flour, pumice, tripoli, wood flour, walnut shell flour, redwood flour and lignin.

As stated, it is frequently desirable to incorporate a surface-active agent in the compositions of the present invention. Such surface-active or wetting agents are advantageously employed in both the solid and liquid compositions. The surface-active agent can be anionic, cationic or nonionic in character.

Typical classes of surface-active agents include alkyl sulfonate salts, alkylaryl sulfonate salts, alkylaryl polyether alcohols, fatty acid esters of polyhydric alcohols and the alkylene oxide addition products of such esters, and addition products of long-chain mercaptans and alkylene oxides. Typical examples of such surface-active agents include the sodium alkylbenzene sulfonates having 10 to 18 carbon atoms in the alkyl group, alkyl phenol ethylene oxide condensation products, e.g., p-isooctylphenol condensed with 20 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decyl sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutylnaphthalene sulfonate, sodium lignin sulfonate, polyethylene glycol stearate, sodium dodecyl benzene sulfonate, tertiary dodecyl polyethylene glycol thioether (nonionic 218), long-chain ethylene oxide-propylene oxide condensation products, e.g., Pluronic 61 (molecular weight about 1000), polyethylene glycol ester of tall oil acids, sodium octophenoxyethoxyethyl sulfate, tris(polyoxyethylene)sorbitan monostearate (Tween 60), and sodium dihexylsulfosuccinate.

The concentration of the active ingredients in solid or liquid compositions generally is from about 0.003 to about 95 percent by weight of more. Concentrations from about 0.05 to about 50 percent by weight are often employed. In compositions to be employed as concentrates, the active ingredient can be present in a concentration from about 5 to about 98 weight percent, preferably 15–50 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

The present compositions can be applied by the use of power dusters, boom and hand sprayers, spray dusters, by addition to irrigation water, and by other conventional means. The compositions can also be applied from airplanes as a dust or spray since the active ingredients are effective at very low application rates.

The active ingredients of the present invention have been found to possess desirable herbicidal activity in general against grassy weeds such as foxtail, barnyard grass, wild oats and crabgrass in preemergent operations and also against the same grasses and particularly seedling Johnson grass in postemergent operations. These compounds possess unique activity in being effective in the control broadly of all or most of Johnson grass, quack grass, bermuda grass, orchard grass, Dallis grass and cogon grass, all perennial grassy weeds, while being tolerant to fairly tolerant to broadleaf crops such as cotton and soybeans.

The active ingredients of the present invention have been found to possess particularly desirable herbicidal activity against wild oats, foxtail, barnyard grass, crabgrass and seedling Johnson grass in postemergent operations, as well as desirable broad spectrum activity against the perennial grassy weeds listed above and at lower dosage rates than the substituted propanoates and propanols of the prior art while showing a greater tolerance to broad leaf crops.

The present compounds which are substituted propanols or propyl ethers are more effective in preemergent operations than in postemergent applications.

The exact rate to be applied is dependent not only on a specific active ingredient being applied, but also on a particular action desired (e.g., general or selective control), the plant species to be modified and the stage of growth thereof as well as the part of the plant to be contacted with the toxic active ingredient. Thus, it is to be understood that all of the active ingredients of the present invention and compositions containing the same may not be equally effective at similar concentrations or against the same plant species. In non-selective pre-emergence and foliar treatments, the active ingredients of the invention are usually applied at an approximate rate of from about 0.5 to about 5 pounds/acre, but lower or higher rates may be appropriate in some cases such as 0.01 to about 20 pounds/acre or more. In preemergent operations for selective uses a dosage of about 0.01 to about 10 pounds/acre or more is generally applicable, a rate of 0.05 to 4 pounds/acre being preferred and about 0.1 to about 2 pounds/acre being most preferred. For controlling an infestation of annuals, a dosage of about 0.1 to 0.5 pound/acre is generally utilized. When the infestation consists largely of perennials, a dosage of from 0.1 to 4, preferably 0.5 to 2.0 pounds/acre should be employed.

In postemergent operations a dosage of about 0.01 to about 20 pounds/acre or more is generally applicable, although not all compounds are equally effective and some weeds are more difficult to control. A dosage rate in the range of about 0.05 to about 0.75 pounds/acre is preferred in selective postemergent control of annual grassy weeds, while about 0.5 to about 5 pounds/acre is preferred and more preferably about 0.5 to about 2 pound/acre for the selective postemergent control of perennial grassy weeds.

In view of the foregoing and the following disclosures, one skilled in the art can readily determine the optimum rate to be applied in any particular case.

In representative operations, each compound to be utilized in a series of tests is dissolved in acetone to one half of the final volume (twice the final concentration) to be used and the acetone solution in each case is admixed with an equal volume of water containing 0.1 percent by weight of Tween-20 surface active material (Tween-20 is a trademark of Atlas Chemical Company). Each compound is selected from a group consisting of compounds according to the invention. The compositions, generally in the nature of an emulsion, were employed to treat separate respective seed beds of sandy loam soil of good nutrient content wherein each seed bed contained separate groups of a known number of good viable seeds, each group being of one of a predetermined plant species. The various beds were positioned side by side and exposed to substantially identical conditions of temperature and light. Each bed was maintained so as to prevent any interaction with test compounds in different seed beds. Each seed bed was treated with one of the compositions as a soil drench applied at one of two predetermined rates to deposit a predetermined amount of a given test compound uniformly throughout the surface of the bed. The compositions were applied to the seed beds so that different seed beds of a given plant species were treated with one of each of the test compounds. Another seed bed was treated only with the acetone-Tween-20 water mixture with no chemical added to serve as a control. After treatment, the seed beds were maintained for two weeks under greenhouse conditions conducive for good plant growth and watered as necessary. The specific plant species, test compound and dosage and the percent preemergent control obtained are set forth in Table I below. Control refers to the reduction in growth compared to the observed results of the same species.

TABLE I

Preemergence Control of Plant Species, %

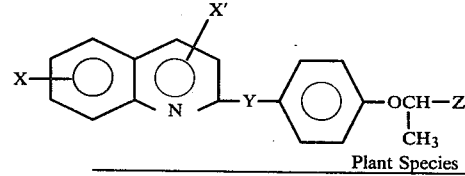

| Compound Tested | | | | Dosage in Lbs Per Acre | Plant Species | | | | | | | | |
|---|---|---|---|---|---|---|---|---|---|---|---|---|---|
| X | X' | Y | Z | | Corn | Rice | Sorghum | Wheat | Barn-yard Grass | Crab-Grass | Fox-tail | Johnson grass | Wild Oats |
| 6-Cl | H | O | —COOH | 2 | 100 | 100 | 100 | 100 | 100 | 100 | 100 | 100 | 70 |
| | | | | 1 | 80 | 100 | 100 | 70 | 100 | 100 | 100 | 100 | 100 |
| | | | | .5 | 40 | 100 | 100 | 20 | 100 | 100 | 100 | 100 | 97 |
| | | | | .25 | 0 | 0 | 100 | 100 | 100 | 100 | 100 | 100 | 95 |
| | | | | .125 | 0 | 0 | 100 | 0 | 70 | 40 | 80 | 80 | 30 |
| 6-Br | H | O | —COOH | 4 | 90 | 50 | 100 | 60 | 100 | 100 | 100 | 100 | 30 |
| | | | | 2 | 80 | 98 | 100 | 30 | 80 | 100 | 100 | 100 | 98 |
| | | | | 1 | 80 | 30 | 100 | 20 | 80 | 100 | 100 | 90 | 60 |
| | | | | .5 | 70 | 0 | 100 | 0 | 60 | 100 | 100 | 80 | 30 |
| | | | | .25 | 60 | 0 | 80 | 0 | 20 | 100 | 100 | 30 | 0 |
| 6-F | H | O | —COOH | 1 | 100 | 100 | 100 | 100 | 100 | 100 | 100 | 100 | 98 |
| | | | | .5 | 98 | 100 | 100 | 100 | 100 | 95 | 100 | 100 | 80 |
| | | | | .25 | 95 | 100 | 100 | 80 | 100 | 95 | 100 | 100 | 60 |
| | | | | .125 | 80 | 80 | 90 | 60 | 98 | 95 | 80 | 95 | 30 |
| | | | | .063 | 70 | 50 | 40 | 30 | 50 | 30 | 60 | 90 | 30 |
| 6-Cl | 3-Cl | O | —COOH | 4 | 40 | 20 | 60 | 20 | 100 | 70 | 80 | 80 | 70 |
| | | | | 2 | 40 | 0 | 70 | 0 | 99 | 90 | 20 | 30 | 20 |
| | | | | 1 | 10 | 0 | 20 | 0 | 80 | 30 | 0 | 0 | 0 |
| | | | | .5 | 0 | 0 | 20 | 0 | 0 | 0 | 0 | 0 | 0 |

TABLE I-continued

Preemergence Control of Plant Species, %

$$X\text{—}\underset{N}{\underset{|}{\bigcirc\bigcirc}}\overset{X'}{\underset{|}{|}}\text{—}Y\text{—}\bigcirc\text{—}O\underset{CH_3}{\overset{|}{C}H}\text{—}Z$$

| Compound Tested | | | | Dosage in Lbs | Plant Species | | | | | | | | |
|---|---|---|---|---|---|---|---|---|---|---|---|---|---|
| X | X' | Y | Z | Per Acre | Corn | Rice | Sorghum | Wheat | Barn-yard Grass | Crab-Grass | Fox-tail | Johnson grass | Wild Oats |
| | | | | .25 | 0 | 0 | 0 | 0 | 0 | 0 | 0 | 0 | 0 |

On repeating the foregoing test procedures using other substituted propionic acids of the invention and the plants. The results are tabulated below in Table II.

TABLE II

Postemergence Control of Plant Species, %

$$X\text{—}\underset{N}{\underset{|}{\bigcirc\bigcirc}}\overset{X'}{\underset{|}{|}}\text{—}Y\text{—}\bigcirc\text{—}O\underset{CH_3}{\overset{|}{C}H}\text{—}Z$$

| Compound Tested | | | | Dosage PPM | Corn | Rice | Sorghum | Wheat | Wild oats | Fox-tail | Barn-yard grass | Crab-grass | Johnson grass |
|---|---|---|---|---|---|---|---|---|---|---|---|---|---|
| X | X' | Y | Z | | | | | | | | | | |
| H | H | O | —COOH | 2000 | 90 | 70 | 70 | 70 | 40 | 98 | 100 | 60 | 98 |
| | | | | 1000 | 100 | 70 | 0 | 90 | 40 | 75 | 100 | 60 | 98 |
| | | | | 500 | 100 | 60 | 0 | 80 | 40 | 90 | 100 | 60 | 95 |
| | | | | 250 | 98 | 40 | 0 | 90 | 0 | 90 | 98 | 30 | 95 |
| | | | | 125 | 95 | 0 | 0 | 60 | 0 | 90 | 98 | 0 | 90 |
| | | | | 62.5 | 98 | 0 | 0 | 40 | 0 | 90 | 90 | 0 | 40 |
| 6-F | H | O | —COOH | 500 | 100 | 95 | 100 | 100 | 100 | 100 | 100 | 100 | 100 |
| | | | | 250 | 100 | 70 | 100 | 100 | 100 | 100 | 100 | 100 | 100 |
| | | | | 125 | 100 | 100 | 100 | 100 | 100 | 100 | 100 | 100 | 100 |
| | | | | 62.5 | 100 | 40 | 100 | 100 | 100 | 100 | 100 | 100 | 100 |
| | | | | 31.25 | 100 | 20 | 100 | 100 | 80 | 100 | 100 | 100 | 100 |
| | | | | 15.6 | 50 | 0 | 80 | 90 | 70 | 100 | 100 | 80 | 95 |
| 6-Br | H | O | —COOH | 250 | 80 | 30 | 80 | 80 | 70 | 100 | 100 | 100 | 100 |
| | | | | 125 | 90 | 10 | 90 | 90 | 40 | 98 | 100 | 100 | 100 |
| | | | | 62.5 | 80 | 0 | 70 | 95 | 50 | 100 | 99 | 99 | 100 |
| | | | | 31.25 | 90 | 0 | 70 | 90 | 0 | 98 | 100 | 98 | 100 |
| | | | | 15.6 | 90 | 0 | 20 | 90 | 0 | 80 | 100 | 98 | 100 |
| | | | | 7.8 | 20 | 0 | 0 | 20 | 0 | 60 | 98 | 90 | 98 | the metal and amine salts, esters, amides, nitriles, propanols, esters of the propanols and propanol ethers herein embraced substantially the same fine preemergent herbicidal results are obtained.

So as to illustrate clearly the phytotoxic properties of the various active ingredients of the present invention applied postemergently, a group of controlled greenhouse experiments is described below.

Various species of plants were planted in beds of good agricultural soil in a greenhouse. After the plants had emerged and grown to a height of about 2-6 inches a portion of the plants were sprayed with an aqueous mixture, made by mixing a selected active ingredient and emulsifier or dispersant with about 1:1 water-acetone, employing sufficient amounts of the treating composition to provide application rates of 4000 parts per million (ppm) or about 10 pounds per acre and in some cases at lower rates. Other plants were sprayed only with the aqueous mixture containing no active ingredient to serve as controls.

After a period of 2 weeks, the effect of the respective test ingredient used on respective groups of plants was evaluated by a comparison with the control groups of In preemergent operations carried out in a manner similar to that described above, using 10 pounds/acre of active ingredient, 2-(4-((6-bromo-2-quinolinyl)thio)-phenoxy propionic acid gave 60 percent control of wild oats, 100 percent control of foxtail, crabgrass and pigweed and 98 percent control of barnyard grass.

In postemergent operations carried out as described above, using 4000 ppm, this compound gave 20 percent conrol of wild oats and no control of the foxtail, crabgrass, pigweed or barnyard grass.

In further postemergent operations, 2-(4-((3,6-dichloro-2-quinolinyl)oxy)phenoxy)propionic acid, employing 4000 ppm, gave 20 percent control of wild oats and 80 percent control of barnyard grass and crabgrass. There was no control of foxtail.

On repeating the foregoing test procedures using the other substituted propanoic acids of the invention and the metal and amine salts, esters, amides, nitriles, propanols, esters of the propanols and propanol ethers herein embraced, substantially the same fine postemergent herbicidal results are obtained.

What is claimed is:

1. A compound of the formula:

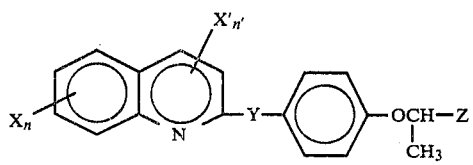

wherein
X and X' are independently F, Cl, Br, I, CF$_3$—, CH$_3$O—, —NO$_2$, or —N(R')$_2$; with the proviso that both cannot be CF$_3$—, CH$_3$O—, —NO$_2$, or —NR'$_2$;
n is 0, 1 or 2;
n' is 0 or 1;
Y is O or S;
Z is —CO$_2$H, —CO$_2$M, —CO$_2$R, —COSR, —CONR'$_2$, —CSNH$_2$, —CN, —CH$_2$OR' or —CH$_2$O$_2$CR';
M is Na, K, Mg, Ca or —N(R'')$_4$;
R'' is H, C$_1$-C$_4$ alkyl or C$_2$-C$_3$ hydroxyalkyl;
each R' is independently H or C$_1$-C$_4$ alkyl; and
R is C$_1$-C$_8$ alkyl or C$_3$-C$_6$ alkoxyalkyl.

2. The compound according to claim 1 wherein X is F, Cl, Br or I; n is 1 or 2, n' is 0; Y is O and Z is —CO$_2$H, —CO$_2$M or —CO$_2$R.

3. The compound according to claim 2 wherein Z is —COOH.

4. The compound according to claim 3 wherein X is 6-chloro.

5. The compound according to claim 3 wherein X is 6-bromo.

6. The compound according to claim 3 wherein X is 6-fluoro.

7. The compound according to claim 1 wherein X is 6-chloro, X' is 3-chloro, Y is oxygen and Z is —COOH.

8. The compound according to claim 1 wherein X is F, Cl, Br, or I, n is 1 or 2, n' is 0, Y is sulfur and Z is —CO$_2$H, —CO$_2$M, or —CO$_2$R.

9. The compound according to claim 8 wherein X is 6-bromo and Z is —CO$_2$H.

10. The compound according to claim 8 wherein X is 6-chloro and Z is —CO$_2$H.

11. A composition comprising an inert agricultural carrier and a herbicidally effective amount in the range of from about 0.003 percent by weight to about 95 percent by weight of a compound having the formula:

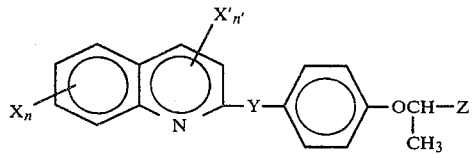

wherein
X and X' are independently F, Cl, Br, I, —CF$_3$, CH$_3$O—, —NO$_2$, or —N(R')$_2$; with the proviso that both cannot be —CF$_3$, CH$_3$O—, —NO$_2$, or —NR'$_2$;
n is 0, 1 or 2;
n' is 0 or 1;
Y is O or S;
Z is —CO$_2$H, —CO$_2$M, —CO$_2$R, —COSR, —CONR'$_2$, —CSNH$_2$, —CN, —CH$_2$OR' or —CH$_2$O$_2$CR';
M is Na, K, Mg, Ca or —N(R'')$_4$;
R'' is H, C$_1$-C$_4$ alkyl or C$_2$-C$_3$ hydroxyalkyl;
each R' is independently H or C$_1$-C$_4$ alkyl; and
R is C$_1$-C$_8$ alkyl or C$_3$-C$_6$ alkoxyalkyl.

12. The composition according to claim 11 wherein X is F, Cl, Br, or I; n is 1 or 2, n' is 0; Y is O; and Z is —CO$_2$H, —CO$_2$M or —CO$_2$R.

13. The composition according to claim 12 wherein Z is —CO$_2$H.

14. The composition according to claim 13 wherein X is 6-chloro.

15. The composition according to claim 13 wherein X is 6-bromo.

16. The composition according to claim 13 wherein X is 6-fluoro.

17. The composition according to claim 11 wherein X is 6-chloro, X' is 3-chloro, Y is oxygen and Z is —COOH.

18. The composition according to claim 11 wherein X is F, Cl, Br, or I, n is 1 or 2, n' is 0, Y is sulfur and Z is —CO$_2$H, —CO$_2$M, or —CO$_2$R.

19. The composition according to claim 18 wherein X is 6-bromo and Z is —CO$_2$H.

20. The composition according to claim 18 wherein X is 6-chloro and Z is —CO$_2$H.

21. The method of controlling undesired plant growth which comprises applying to the locus of said plants a herbicidally effective amount in the range of from 0.01 to 20 lbs/acre of a compound having the formula:

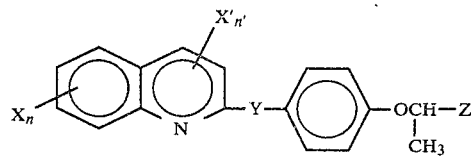

wherein
X and X' are independently F, Cl, Br, I, —CF$_3$, CH$_3$O—, —NO$_2$, or —N(R')$_2$; with the proviso that both cannot be —CF$_3$, CH$_3$O—, —NO$_2$, or —NR'$_2$;
n is 0, 1 or 2;
n' is 0 or 1;
Y is O or S;
Z is —CO$_2$H, —CO$_2$M, —CO$_2$R, —COSR, —CONR'$_2$, —CSNH$_2$, —CN, —CH$_2$OR' or —CH$_2$O$_2$CR';
M is Na, K, Mg, Ca or —N(R'')$_4$;
R'' is H, C$_1$-C$_4$ alkyl or C$_2$-C$_3$ hydroxyalkyl;
each R' is independently H or C$_1$-C$_4$ alkyl; and
R is C$_1$-C$_8$ alkyl or C$_3$-C$_6$ alkoxyalkyl.

22. The method according to claim 21 wherein X is F, Cl, Br or I; n is 1 or 2; n' is 0; Y is O and Z is —CO$_2$H, —CO$_2$M, or —CO$_2$R.

23. The method according to claim 22 wherein X is —CO$_2$H.

24. The method according to claim 23 wherein X is 6-chloro.

25. The method according to claim 23 wherein X is 6-bromo.

26. The method according to claim 23 wherein X is 6-fluoro.

27. The method according to claim 21 wherein X is 6-chloro, X' is 3-chloro, Y is oxygen and Z is —CO$_2$H.

28. The method according to claim 21 wherein X is F, Cl, Br or I; n is 1 or 2; n' is 0; Y is sulfur and Z is —$CO_2H$.

29. The method according to claim 28 wherein X is 6-bromo and Z is —$CO_2H$.

30. The method according to claim 28 wherein X is 6-chloro and Z is —$CO_2H$.

31. The method according to claim 21 wherein the compound is applied in preemergent operations in an amount of from 0.05 to 4 pounds per acre.

32. The method of claim 31 wherein the compound employed is 2-(4-((6-chloro-2-quinolinyl)oxy)phenoxy)-propionic acid.

33. The method according to claim 21 wherein the compound is applied in postemergent operations in an amount of from 0.5 to 5 pounds per acre.

34. The method of claim 33 wherein the compound employed is 2-(4-((6-fluoro-2-quinolinyl)oxy)phenoxy)-propionic acid.

* * * * *

UNITED STATES PATENT AND TRADEMARK OFFICE
CERTIFICATE OF CORRECTION

PATENT NO. : 4,236,912

DATED : December 2, 1980

INVENTOR(S) : Howard Johnston; Lillian H. Troxell; Jon S. Claus

It is certified that error appears in the above—identified patent and that said Letters Patent is hereby corrected as shown below:

The title of the patent should read --QUINOLINYLOXYPHENOXY AND QUINOLINYLTHIOPHENOXY ALKANOIC ACIDS AND DERIVATIVES THEREOF AND METHODS OF HERBICIDAL USE--.

Abstract, next to last line, delete "useul" and insert --useful--.

Column 3, line 45, delete "2-haloquoinoline" and insert --2-haloquinoline--.

Column 10, line 34, delete "of" and insert --or--.

Column 13, line 67, delete "ingredient" and insert --ingredients--.

Signed and Sealed this

Seventeenth Day of March 1981

[SEAL]

Attest:

RENE D. TEGTMEYER

Attesting Officer

Acting Commissioner of Patents and Trademarks